United States Patent [19]

Danielsson et al.

[11] Patent Number: 5,427,110
[45] Date of Patent: Jun. 27, 1995

[54] CIRCUIT ARRANGEMENT FOR THE PROCESSING OF PHYSIOLOGICAL MEASUREMENT SIGNALS

[75] Inventors: Peter Danielsson, Bromma; Thomas Ohlsson, Vallingby, both of Sweden

[73] Assignee: Siemens Aktiengesellschaft, Munich, Germany

[21] Appl. No.: 108,749

[22] PCT Filed: Mar. 4, 1992

[86] PCT No.: PCT/EP92/00475
§ 371 Date: Dec. 22, 1993
§ 102(e) Date: Sep. 3, 1993

[87] PCT Pub. No.: WO92/15244
PCT Pub. Date: Sep. 17, 1992

[30] Foreign Application Priority Data

Mar. 4, 1991 [DE] Germany .................. 41 06 857.2

[51] Int. Cl.6 .......................... A61B 5/0428
[52] U.S. Cl. .................. 128/696; 128/902; 128/905
[58] Field of Search ............... 128/696, 702, 901, 902, 128/905

[56] References Cited

U.S. PATENT DOCUMENTS 4,530,365 7/1989 Harada et al. .................. 128/696

Primary Examiner—Lee S. Cohen
Assistant Examiner—Jeffrey R. Jastrzab
Attorney, Agent, or Firm—Hill, Steadman & Simpson

[57] ABSTRACT

Circuit arrangement for the processing of physiological measurement signals. In a known circuit arrangement, each one of a plurality of electrodes for picking up physiological measurement signals connects with a first input connection of an input amplifier associated with the pertinent electrodes; the input amplifiers connect, at their respective second input connections, with a common reference potential connection. To check the functional capability of the input amplifiers, a calibration pulse generator connects on the output side with one of the electrodes and the reference potential connection. In addition, to check the electrodes (1, 2, 3) and their supply lines, an additional amplifier (24) connects, by its input, with the reference potential connection (7) and, at its output, with an additional electrode (25) on the patient. By this means, a component of the calibration pulse reaches the electrodes (1, 2, 3) via the body resistance of the patient and thus permits the checking of said electrodes for a defect.

1 Claim, 1 Drawing Sheet

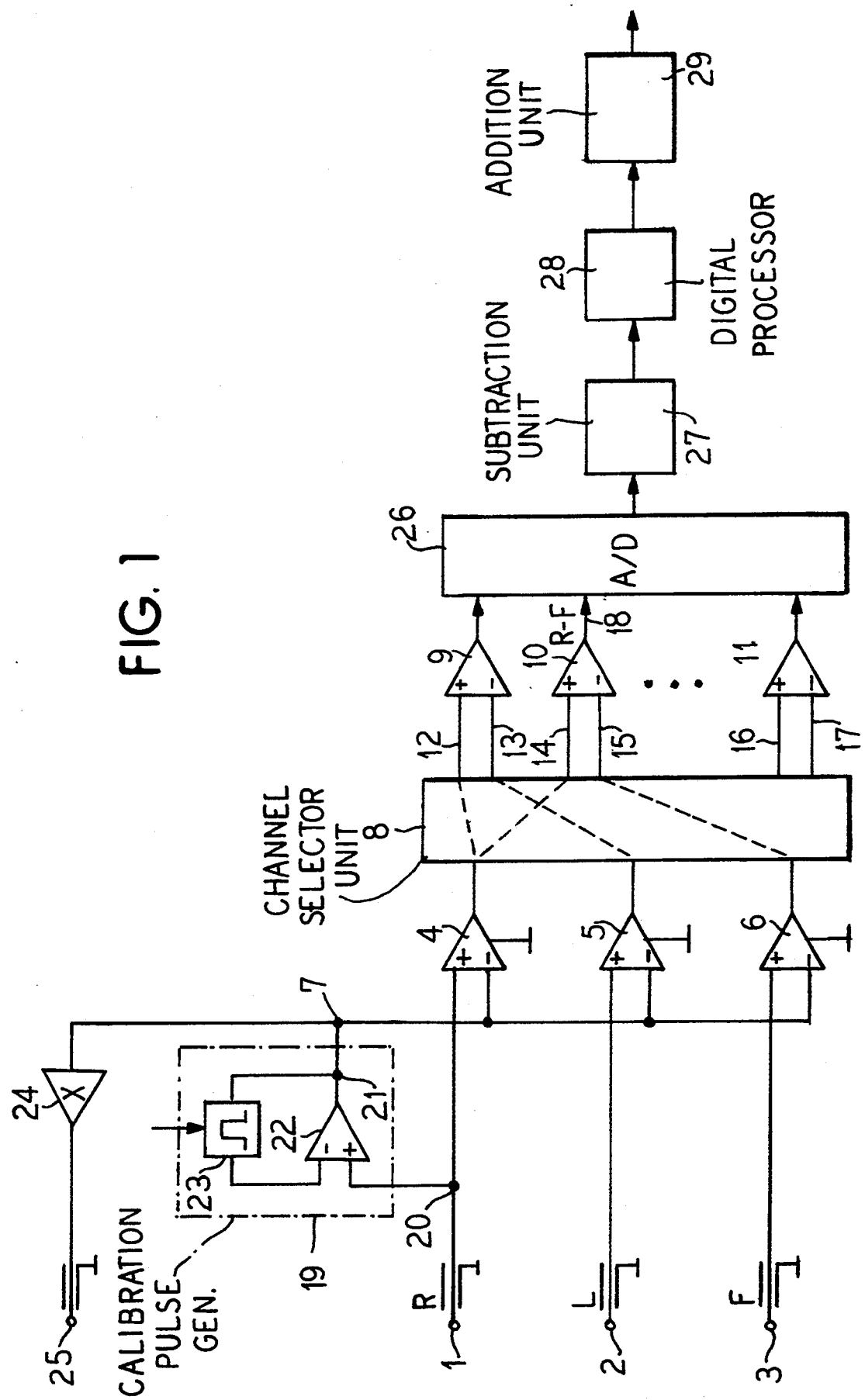

CIRCUIT ARRANGEMENT FOR THE PROCESSING OF PHYSIOLOGICAL MEASUREMENT SIGNALS

The invention relates to a circuit arrangement for the processing of physiological measurement signals, which are taken by means of electrodes on a patient, having input amplifiers which are individually associated with the electrodes and which are each connected at a first input connection with the electrodes associated with them and at a second input connection with a common reference potential connection. A device is disposed downstream of the input amplifiers on the output side, for the formation of difference signals from the output signals each of two selectable input amplifiers. A calibration pulse generator is connected with one of the electrodes and the reference potential connection and generates a calibration pulse between the two.

DESCRIPTION OF THE RELATED ART

In such a circuit arrangement known from German Patent 2,429,955, the calibration pulse-generator generates a calibration pulse of defined height and duration between the input connections of the individual input amplifiers. In a device disposed downstream of the input amplifiers on the output side, difference signals are formed from the output signals of two selectable input amplifiers, so that the calibration pulse does not appear in the pertinent difference signals, on account of the difference formation. However, if one of the input amplifiers is defective, a pulse-type output error signal results in formation of the difference signals. In the known circuit arrangement, it is possible to detect defects in the input amplifiers, but not defects, which may occur at the electrodes and in their supply lines to the input amplifiers.

SUMMARY OF THE INVENTION

It is an object of the present invention is to improve the known circuit arrangement so that a testing of the electrodes and their supply lines to the input amplifiers is also possible.

According to the invention, this object is inventively achieved with the circuit arrangement of the initially indicated type having an additional amplifier connected by its input to the reference potential connection, and the output connection of the additional amplifier connected to an additional electrode on the patient. Upon the emission of a calibration pulse by the calibration pulse generator, a pulse component defined by the gain of the additional amplifier is fed to the patient via the additional electrode, while the reference potential connection is acted upon by the residual pulse component. Since all electrodes disposed on the body of the patient electrically connect with one another via the body impedance, the pulse component fed to the patient appears at all these electrodes. In the course of the subsequent formation of difference signals from the output signals of two selected input amplifiers, the pertinent pulse component is suppressed and accordingly does not appear. If, however, a defect occurs in the input amplifier which has participated in the formation of the different signal or in the electrode supply line between the input amplifier and the associated electrode, or if the pertinent electrode has faulty contact with the body of the patient, then this defect is expressed in the form of an output pulse in the difference signal.

In an advantageous refinement of the circuit arrangement according to the invention, downstream of the outputs of the input amplifiers there is disposed a device for digital signal processing. In this device, prior to the actual signal processing of the output signals of the input amplifiers, the calibration pulse is subtracted and is added again to the signals after their digital processing. In this manner, the calibration pulse is excluded from the signal processing, so that, especially when using digital filters, these do not need to be designed to account for the calibration pulse. The frequency content of the calibration pulse differs considerably from that of the physiological measurement signals.

BRIEF DESCRIPTION OF THE DRAWINGS

The exemplary embodiments of the apparatus for a circuit arrangement for the processing of physiological measurement signals of the present invention shall be set forth in greater detail below with reference to the drawing.

FIG. 1 shows an illustrative embodiment of the present invention.

DESCRIPTION OF THE PREFERRED EMBODIMENTS

FIG. 1 shows an embodiment of the present invention having three input channels R, L and F which lead to three electrodes 1, 2 and 3 which are placed on the body of the patient (not shown here) and specifically on the right (R) and left (L) arm and on the left foot (F). In addition to these three input channels R, L and F, there are in known manner also further input channels for electrodes on the thoracic wall of the patient, which however, for the sake of clarity, are not shown here. With each one of the electrodes 1, 2 and 3 there is associated in each instance an input amplifier 4, 5 and 6, which is designed as a differential amplifier with a first input connection (+) and a second input connection (−). In this embodiment each one of the input amplifiers 4, 5 and 6, has a first input connection (+) connected with associated electrode 1, 2 or 3, and second input connections (−) connected with one another to form a common reference potential connection 7. The input amplifiers 4, 5 and 6 connect on the output side to a channel selector unit 8, via filter stages (not shown here) where appropriate, with a plurality of associated differential amplifiers 9, 10 and 11. The differential amplifiers 9, 10 and 11 each have two inputs 12 and 13, 14 and 15, or 16 and 17. In this embodiment, the output signals of two input amplifiers selected by the channel selector unit 8, e.g. 4 and 6, can be fed to each input pair, e.g. 14 and 15. Thus, in the case of the example shown, the difference signal R-F is formed at the output 18 of the differential amplifier 10.

Between the two input connections (+) and (−) of the input amplifier 4 associated with the channel R or the electrode designated by 1, a calibration pulse generator is connected 19, which generates between its two connections 20 and 21, on demand, a voltage pulse of defined height (preferably 1 mV) and duration. To avoid electrically loading the channel R, the calibration pulse generator 19 is designed as an impedance converter 22 with a voltage pulse emitter 23 in the feedback branch. At the reference potential connection 7, which is common to all input amplifiers 4, 5 and 6, there is therefore present a potential which corresponds to the potential at the electrode 1 overlaid with the voltage pulse of the calibration pulse generator 19. Accordingly, this potential is overlaid with the same disturbance signals which are detected by the electrodes 1, 2 and 3. Since the input amplifiers 4, 5 and 6 are differential amplifiers, these disturbance signals are not amplified, but suppressed. When a calibration pulse is generated, the reference potential for all input amplifiers 4, 5 and 6 is altered at the connection 7 in the same manner. Since the difference between the two output signals of the input amplifiers 4, 5 and 6 is formed by the differential amplifiers 9, 10 and 11. No. alteration of the output signals of the differential amplifiers 9 to 11 results from the alteration of the reference potential at the connection 7, as long as the input amplifiers 4, 5 and 6 are operating properly. On the other hand, if one of the input amplifiers 4, 5 and 6 is defective, then an output defect signal appears at that one of the differential amplifiers that received an input signal from the defective input amplifier.

If, by way of example, the voltage generated by the calibration pulse generator 19 between the connections 20 and 21 is designated by U, and if the potentials taken off from the electrodes 1, 2 and 3 are designated by R, L and F, then the potential at the reference potential connection 7 has the value R-U and the input voltages U, L-R+U and F-R+U are present between the input connections (+) and (−) of the input amplifiers 4, 5 and 6. Thus, given the input amplifiers 4, 5 and 6 are in order, between the output signals of the input amplifiers 4 and 5 is the difference signal L-R, between the input amplifiers 5 and 6 is the difference signal L-F and between the input amplifiers 4 and 6 is the difference signal F-R.

The circuit arrangement shown in FIG. 1 corresponds—as described up to this point—to the arrangement known from German Patent 2,429,955. As the former description indicates, defects in the input amplifiers 4, 5 and 6 may be detected, but not at the electrodes 1, 2 and 3 and their supply lines to the input amplifiers 4, 5 and 6. In order to achieve this, an additional amplifier 24 connects, by its input, to the reference potential connection 7 and, at its output, with an additional electrode 25, which is disposed on the body of the patient, e.g. on his right foot. In this manner, the potential present at the reference potential connection 7 is amplified and fed to the body of the patient via the electrode 25. If, in this case, the voltage pulse generated by the calibration pulse generator is designated by U and the gain of the amplifier 24 is indicated by x, then the patient is acted upon by a pulse component of the height $U.x/(x-1)$, while the pulse component appearing at the reference potential connection 7 exhibits the height $U/(x-1)$. Since the electrodes 1, 2, 3 and 25 are electrically conductively connected with one another via the body impedance of the patient, the pulse component $U.x/(x-1)$ appears at all electrodes 1, 2, 3 and 25. Since, furthermore, upon the occurrence of the calibration pulse the potential conditions at the electrodes 1, 2 and 3 alter in the same direction and to the same extent as at the reference potential connection 7, as already shown hereinabove, the input voltages U, L-R+U and F-R+U appear at the input amplifiers 4, 5 and 6, so that the difference signals between the outputs of the input amplifiers 4 and 5, 5 and 6, and 4 and 6, have the unchanged values of L-R, L-F and F-R respectively. If, however, a defect appears in one of the input amplifiers 4, 5 or 6 or in one of the electrode supply lines between the input amplifiers 4, 5 and 6 and the electrodes 1, 2 and 3, or if one of the electrodes 1, 2 or 3 has faulty contact with the body of the patient, then this defect is expressed in the form of an output pulse at that one of the differential amplifiers 9, 10 and 11 that connects with the pertinent defective channel R, L or F via the channel selector unit 8.

In the illustrative embodiment shown, the formation of difference signals from the output signals of the input amplifiers 4, 5 and 6 takes place in an analogous manner. The manner in which the functional capability of the differential amplifiers 9, 10 and 11 can also be checked is evident from the already cited German Patent 2,429,955. By way of an alternative to the analog signal processing, the output signals of the input amplifiers 4, 5 and 6 can also be further processed digitally. Since, as has already been described hereinabove, the calibration pulse vanishes only upon the formation of the difference signals from the output signals of the input amplifiers. In the case of digital signal processing the calibration pulse would have to be processed as well in all process steps which precede a difference formation. Especially in the case of digital signal filtering, this would be a disturbing factor, since the calibration pulse exhibits a different frequency spectrum from the physiological signals. Moreover, in the case of a complex signal processing, it would be necessary to draw a distinction as to whether the calibration pulse vanishes or remains otherwise preserved on account of difference formations. Accordingly, after conversion of the output signals of the differential amplifiers 9, 10 and 11 into digital form in an A/D converter 26, the digital signals are supplied to a subtraction unit 27 wherein the calibration pulse is subtracted from the output signals of the input amplifiers 4, 5 and 6. After this, the digital signal processing takes place in a digital processor 28, and at the end thereof a new calibration pulse is added to the digitally processed signals in an addition unit 29. In this manner, the calibration pulse is excluded from the digital signal processing. Only where a defect is present in the input amplifier circuit, does a residual pulse which participates in the signal processing remain after the subtraction.

Although various modifications may be suggested by those versed in the art, it should be understood that we wish to embody within the scope of the patent granted hereon, all such modifications as reasonably and properly come within the scope of our contribution to the art.

We claim:

1. A circuit arrangement for processing physiological measurement signals obtained by a plurality of electrodes interacting with a patient, comprising:

a plurality of electrodes a plurality of input amplifiers respectively individually associated with said electrodes, each input amplifier having a first input connected to the electrode associated therewith and a second input connected to a common reference potential, and each input amplifier having an output at which that input amplifier generates an output signal;

means connected to the outputs of said input amplifiers for forming difference signals from the respective signals at the outputs of two selected ones of said input amplifiers;

calibration pulse generator means connected to one of said electrodes and to said reference potential for generating a calibration pulse between said two selected input amplifiers;

an additional electrode an additional amplifier having an input connected to said reference potential and an output connected to said additional electrode adapted to interact with said patient, said calibration pulse being supplied to said patient via said additional amplifier and said additional electrode and thereby causing said calibration pulse to appear in the respective output signals of said input amplifiers as long as said electrodes and input amplifiers are operating faultlessly; and means connected to said outputs of said input amplifiers for digitally processing said output signals, including means for subtracting said calibration pulse from the respective output signals of said input amplifiers before said digital processing and for adding said calibration pulse to the respective output signals after said digital processing.

* * * * *